(12) United States Patent
Rapach et al.

(10) Patent No.: US 7,547,274 B2
(45) Date of Patent: Jun. 16, 2009

(54) RADIOACTIVE MEMBER AND METHOD OF MAKING

(75) Inventors: Michael Rapach, Carpentersville, IL (US); Kevin Helle, Bartlett, IL (US); Charles E. Shanks, Schaumburg, IL (US); Jay Christopher Reed, Elk Grove, IL (US)

(73) Assignee: Medi-Physics, Inc., Princeton, NJ (US)

( * ) Notice: Subject to any disclaimer, the term of this patent is extended or adjusted under 35 U.S.C. 154(b) by 0 days.

(21) Appl. No.: 11/099,238

(22) Filed: Apr. 5, 2005

(65) Prior Publication Data

US 2006/0058570 A1   Mar. 16, 2006

Related U.S. Application Data

(63) Continuation of application No. 10/415,715, filed as application No. PCT/US01/49879 on Nov. 1, 2001, now Pat. No. 6,905,455.

(60) Provisional application No. 60/245,046, filed on Nov. 1, 2000.

(51) Int. Cl.
*A61N 5/00* (2006.01)

(52) U.S. Cl. .......................................... 600/9

(58) Field of Classification Search .................. 600/1–8; 425/542, 472; 264/0.5, 41
See application file for complete search history.

(56) References Cited

U.S. PATENT DOCUMENTS

| | | | |
|---|---|---|---|
| 2,668,162 A | 2/1954 | Lowe | |
| 2,703,316 A | 3/1955 | Schneider | |
| 2,758,987 A | 8/1956 | Salzberg | |
| 3,297,033 A | 1/1967 | Schmitt et al. | |
| 3,351,049 A | 11/1967 | Lawrence et al. | |
| 3,636,956 A | 1/1972 | Schneider | |
| 3,839,297 A | 10/1974 | Wasserman et al. | |
| 4,052,988 A | 10/1977 | Doddi et al. | |
| 4,141,087 A | 2/1979 | Shalaby et al. | |
| 4,323,055 A | 4/1982 | Kubiatowitz | |
| 4,441,496 A | 4/1984 | Shalaby et al. | |
| 4,452,973 A | 6/1984 | Casey et al. | |
| 4,473,670 A | 9/1984 | Kessidis | |
| 4,510,295 A | 4/1985 | Bezwada et al. | |
| 4,612,923 A | 9/1986 | Kronenthal | |
| 4,646,741 A | 3/1987 | Smith | |
| 4,689,424 A | 8/1987 | Shalaby et al. | |

(Continued)

FOREIGN PATENT DOCUMENTS

EP   0466681 B1   5/1991

(Continued)

OTHER PUBLICATIONS

Tapen, et.al., int. J. Radiation Oncology boil. Phys., vol. 42(5) pp. 1063-1067, 1998.

(Continued)

*Primary Examiner*—Samuel G Gilbert
(74) *Attorney, Agent, or Firm*—Robert F. Chisholm (57) ABSTRACT

A radioactive member for use in brachytherapy comprising a molded elongate, bioabsorbable carrier material with spaced radioactive sources disposed therein, and methods for the manufacture thereof. The radioactive members may be used in the treatment of, for example, prostate cancer.

16 Claims, 3 Drawing Sheets

U.S. PATENT DOCUMENTS

| | | |
|---|---|---|
| 4,697,474 A | 10/1987 | Horowitz |
| 4,697,575 A * | 10/1987 | Horowitz ........................ 600/8 |
| 4,702,228 A | 10/1987 | Russell, Jr. et al. |
| 4,741,337 A | 5/1988 | Smith et al. |
| 4,754,745 A * | 7/1988 | Horowitz ........................ 600/8 |
| 4,784,116 A | 11/1988 | Russell et al. |
| 4,815,449 A | 3/1989 | Horowitz |
| 4,916,209 A | 4/1990 | Fung et al. |
| 5,264,540 A | 11/1993 | Cooper et al. |
| 5,404,309 A | 4/1995 | Yamamoto et al. |
| 5,460,592 A * | 10/1995 | Langton et al. ................ 600/7 |
| 5,521,280 A | 5/1996 | Reilly et al. |
| 5,741,522 A | 4/1998 | Violante et al. |
| 6,273,851 B1 * | 8/2001 | Slater et al. ................... 600/8 |

FOREIGN PATENT DOCUMENTS

| | | |
|---|---|---|
| WO | 00/28554 | 5/2000 |
| WO | 00/51136 | 8/2000 |

OTHER PUBLICATIONS

Butler, et.al., Radiation Oncology Investigations 4:48-49, 1996.
J.C. Blasko, et.al., The Urological Clinics of North America, 23, 633-650 (1996).
H. Ragde, et.al., Cancer, 80, 442-453 (1997).

* cited by examiner

RADIOACTIVE MEMBER AND METHOD OF MAKING

This application is a continuation of U.S. application Ser. No. 10/415,715, which issued as U.S. Pat. No. 6,905,455 on Jun. 14, 2005, filed May 1, 2003 which is a filing under 35 U.S.C. 371 of international application No. PCT/US01/49879, filed Nov. 1, 2001, which claims priority to U.S. Provisional application No. 60/245,046 filed Nov. 1, 2000, the entire disclosure of which is hereby incorporated by reference.

FIELD OF THE INVENTION

This invention relates to radiotherapy. More particularly, it relates to radioactive sources for use in brachytherapy and to methods for the preparation of such sources.

BACKGROUND OF THE INVENTION

Brachytherapy is a general term covering medical treatment which involves the placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633-650 (1996), and H. Ragde et al., *Cancer*, 80, 442-453 (1997)). Prostate cancer is one of the most common forms of malignancy in men in the USA, with more than 44,000 deaths in 1995 alone. Treatment may involve the temporary implantation of a radioactive source for a calculated period, followed by its removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half lives and lower energies relative to temporary sources. Examples of permanently implantable sources include iodine-125 or palladium-103 as the radioisotope. The radioisotope is generally encapsulated in a casing such as titanium to form a "seed" which is then implanted. Temporary implants for the treatment of prostate cancer may involve iridium-192 as the radioisotope.

Conventional radioactive sources for use in brachytherapy include so-called seeds, which are sealed containers, for example of titanium, containing the radioisotope within a sealed chamber but permitting radiation to exit through the container/chamber walls (U.S. Pat. Nos. 4,323,055 and 3,351,049). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

For ease of administration of such sources, a number of systems have been proposed. U.S. Pat. No. 4,815,449 discloses a substantially non-deflecting, linear, elongated member for insertion in tumours and made of a bioabsorbable material in the form of a needle or thin pointed cylinder with a plurality of radioactive seeds disposed therein in a predetermined array.

U.S. Pat. No. 5,460,592 discloses a method and apparatus for transporting a radioactive device. The device comprises a flexible, elongated woven or braided bio-absorbable carrier material having spaced radioactive seeds disposed therein. On heating, the carrier material holding the seeds becomes semi-rigid. A length of the semi-rigid carrier material with radioactive seeds disposed therein may then be loaded into a conventional, hollow metal dispensing needle or applicator cartridge which is used to implant the radioactive seeds into or contiguous to the treatment site, for example a tumour.

A commercial product consisting of iodine-125 seeds regularly spaced at between 0.6 and 1.2 cm centre to centre inside a braided, semi-rigid bioabsorbable suture material is available from Medi-Physics Inc. under the trade name I-125 RAPID Strand™. This product may be used to treat conditions such as head and neck cancers, including those of the mouth, lips and tongue, brain tumours, lung tumours, cervical tumours, vaginal tumours and prostate cancer.

One advantage of this type of semi-rigid carrier is that the radioactive seeds are implanted or inserted into a patient with a pre-determined known spacing, depending on their separation in the carrier material. The bioabsorbable material is then slowly absorbed into the patient's body to leave the spaced seeds in position. This predetermined spacing and the semi-rigid nature of the carrier aids a physician in calculating both the total radiation dose and the dose profile which will be delivered by the seeds inside a patient's body, and also aids in accurate placement of the seeds. In addition, more than one seed is implanted at once, so lessening the time taken for implantation over that required for the placement of individual loose seeds. The risk of seed migration away from the site of implantation is also reduced (Tapen et al., *Int. J. Radiation Oncology Biol. Phys.*, vol. 42(5), pages 1063-1067, 1998).

Radioactive sources according to U.S. Pat. Nos. 4,815,449 and 5,460,592 use as little bioabsorbable material as possible to ease absorption but the use of such thin or flexible material has a number of disadvantages. For example, to ensure that the carrier is rigid enough to withstand insertion into the patient's tissues, the carrier material holding the radioactive seeds is stiffened by a heating step during the manufacturing process. However, excessive heat may damage the carrier material, and strict control of the heating and cooling process is critical so as to change the crystalline structure of the carrier material sufficiently to cause stiffening but without causing burning. Even when stiffness is maximised within the possibilities existing within U.S. Pat. No. 5,460,592, the carrier material is not sufficiently rigid to fully guard against jamming of the carrier within the dispensing needle or applicator when in clinical use. Jamming of the carrier within a needle is generally irreversible, so that the needle then has to be disposed of, taking into account the fact that it is now "hot" due to the presence of radioactive seeds. Any adventitious entry of blood and other body fluids into the needle can cause the bioabsorbable material to swell, and strands of the material to fray which also causes jamming of the dispensing needle (Butler et al., *Radiation Oncology Investigations* 4:48-49, 1996). It has, therefore, become common practice for physicians to "plug" the needle in order to prevent the entry of body fluids into the needle during administration. However, if the needles are not well plugged, jamming may still occur. Conversely, jamming can be caused by use of too much plug material or a plug of a very stiff nature which is not easily displaced from the tip of the needle.

The manufacturing process disclosed in U.S. Pat. No. 5,460,592 is also very labour intensive and does not lend itself easily to automation. In addition, each carrier must be visually examined after the stiffening step to ensure that the seeds are securely retained in the braided bioabsorbable material.

Other radioactive members comprise a hollow tube of carrier material (see, for example, U.S. Pat. No. 4,815,449 and EP 0,466,681). In such radioactive members, the position of the radioactive sources within the carrier material may be maintained by the contact and/or elasticity of the carrier material or by introducing non-radioactive fillers or "spacers" into the regions between the radioactive sources. However, the manufacture of such radioactive members is non-trivial, requiring three separate materials (carrier material, radioactive sources and non-radioactive spacers) and the careful assembly of the three in the correct sequence.

There is, therefore, a need for an improved radioactive member which has one or more of the following advantages: provides a more rigid framework, is more resilient to consumer handling, is easier to use and which does not suffer from all the disadvantages of the known sources. Preferably, such an improved radioactive member can be produced using an automated manufacturing process.

SUMMARY OF THE INVENTION

Accordingly, in a first aspect of the invention there is provided a radioactive member for use in brachytherapy comprising an elongate bioabsorbable carrier with spaced radioactive sources disposed therein characterised in that said radioactive member is formed by molding.

In a second aspect of the invention there is provided a radioactive member for use in brachytherapy comprising an elongate bioabsorbable carrier with spaced radioactive sources disposed therein characterised in that said elongate bioabsorbable carrier is of a substantially solid composition.

In a third aspect of the invention there is provided a method for making a radioactive member in accordance with the first or second aspect of the invention. Suitably said method comprises the steps of:
a) providing a mold;
b) introducing a plurality of radioactive sources into the mold;
c) introducing liquid bioabsorbable carrier material into the mold;
d) setting the liquid bioabsorbable carrier material; and
e) removing the set product from the mold.

In yet another embodiment, the polymer may first be introduced into the mold and the radioactive sources subsequently introduced into the molten polymer. The mold then could be opened and the set carrier material, forming a strand, removed. In this embodiment, steps b) and c) of the method of the third aspect of the invention would be reversed.

Accordingly, there is provided a method comprising the steps of:
a) providing a mold;
b) introducing liquid bioabsorbable carrier material into the mold;
c) introducing a plurality of radioactive sources into the mold;
d) setting the liquid bioabsorbable carrier material; and
e) removing the set product from the mold.

The present invention still further contemplates providing a vented mold in which entrapped air may be forced from the mold cavity upon the introduction of the carrier material.

The present invention even still further contemplates employing a foaming or blowing method in molding the polymer in which gas bubbles are introduced into the polymer.

DETAILED DESCRIPTION OF THE PREFERRED EMBODIMENTS

Figure 1:
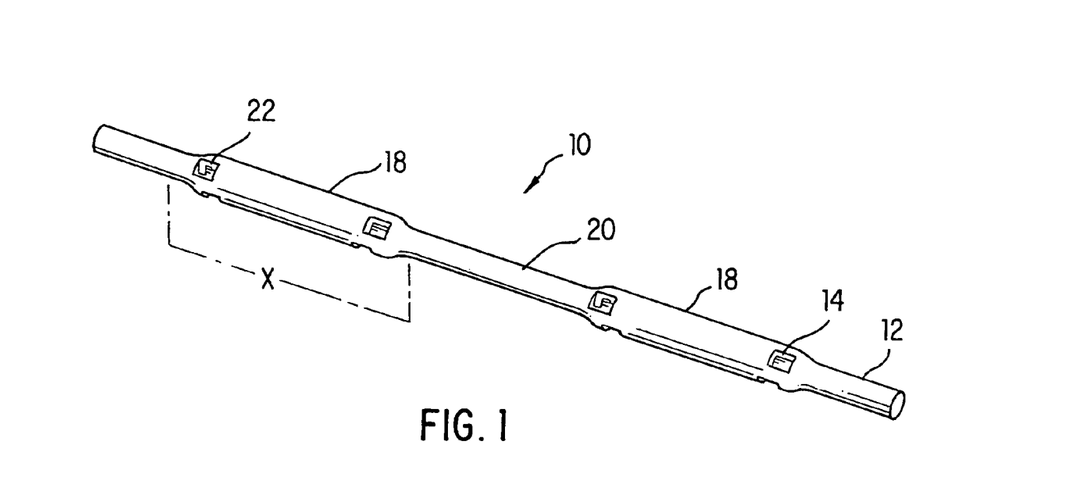
FIG. 1 shows a radioactive member of the present invention.

Referring to FIG. 1, the present invention provides a radioactive member 10 for use in brachytherapy. Radioactive member 10 includes an elongate bioabsorbable carrier 12 with spaced radioactive sources 14 disposed therein. In one embodiment of the present invention, radioactive member 10 is formed by molding. The present invention further contemplates that carrier 12 is of a substantially solid composition.

Figure 2:
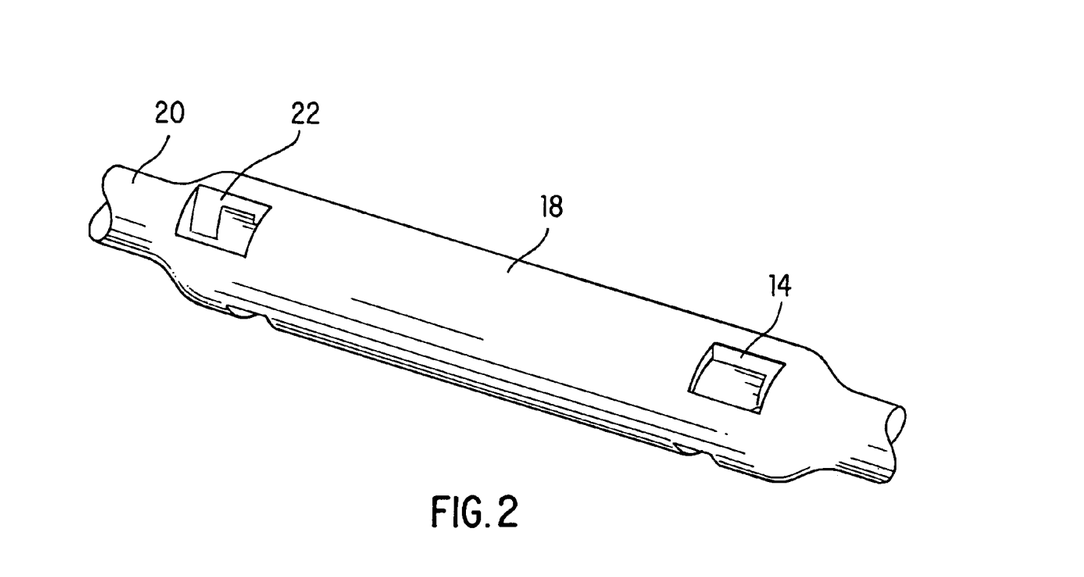
FIG. 2 shows an enlarged view of the radioactive member of FIG. 2, about the section X.

With additional reference to FIG. 2, carrier 12 includes a plurality of seed receiving regions 18 and intermediate regions 20. Carrier 12 may define one or more apertures 22 resulting from a molding process of the present invention in which small pins are positioned at either end of seed receiving regions 18 so as to maintain the location and alignment of the radioactive sources 14 within carrier 12.

Figure 3:
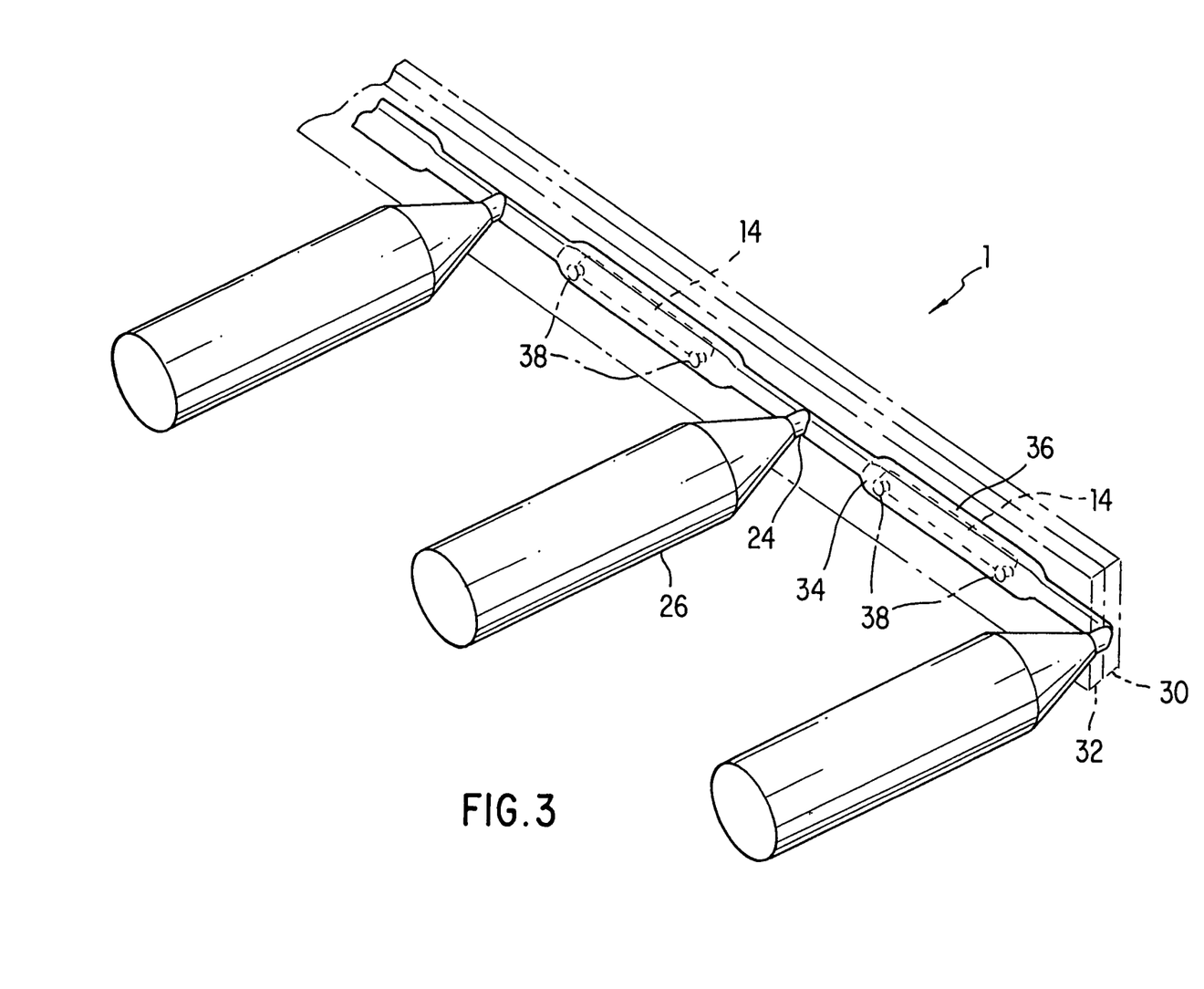
FIG. 3 shows a mold for producing a radioactive member in accordance with the present invention.

In one method of the present invention, a two plate vertical mold is constructed to form a radioactive member 10. FIG. 3 depicts a mold 1 for producing radioactive members of the present invention. Mold 1 includes cooperatively-engageable first and second mold plates 30 and 32. Each of mold plates 30 and 32 define an elongate mold cavity, 34 and 36, for receiving carrier material and a plurality of radiation sources 14. Mold plate 32 includes a plurality of seed positioning pins 38 for positioning and maintaining the radioactive sources 14 during the molding process. The elongate radioactive sources, or seeds, 14 are placed into each seed receiving region 20 and held in place the pins 38 at the end of each seed. The positions of the pins 38 are also indicated by the remaining apertures 22 defined by the molded carrier 12 in FIGS. 1 and 2. The mold is closed and liquid polymer pumped in at each of the injection ports 24 defined in mold plate 32 from injection cannisters 26. The liquid polymer is set prior to the mold being opened and the strand (i.e. elongate bioabsorbable carrier) being removed.

Accordingly, in a first aspect of the invention there is provided a radioactive member for use in brachytherapy comprising an elongate bioabsorbable carrier with spaced radioactive sources disposed therein characterised in that the radioactive member is formed by molding.

In a second aspect of the invention there is provided a radioactive member for use in brachytherapy comprising an elongate bioabsorbable carrier with spaced radioactive sources disposed therein characterised in that the elongate bioabsorbable carrier is of a substantially solid composition.

By "substantially solid" is meant that the bioabsorbable material is disposed essentially continuously throughout the radioactive member. Thus, both the wall of the radioactive member, the region containing the seeds and the gaps between the seeds are the same continuous material i.e. the tubing and spacers are essentially the same single entity with minimal gaps or spaces. Preferably, the radioactive sources will be encapsulated by the bioabsorbable carrier material. This solid nature of the radioactive members of the invention helps to ensure that the spacing of the radioactive sources is maintained for at least a short period post-implantation. This helps to ensure proper dosimetry and minimizes source movement, shedding or migration post implantation. A substantially solid carrier will have improved rigidity compared with the "hollow" or braided tubes of conventional carriers.

The bioabsorbable carrier material may be any non-toxic, bio-compatible, bioabsorbable material or a mixture of such materials. As used herein, a bioabsorbable material is any material of which a substantial portion will be metabolized within a patient's body and ultimately eliminated therefrom. The bioabsorbable material should preferably maintain its integrity once implanted for about 1 to 14 days. Preferably, the carrier material should be fully absorbed by living tissue over a total of about 70 to 120 days.

Molding is a method in which a substantially liquid material is introduced into a mold. When the material sets it takes the shape of the mold. The molding process results in a shaped material having a substantially solid cross section i.e. having material distributed uniformly across its cross section. Thus, particularly preferred bioabsorbable carrier materials which may be used in the radioactive member of the present invention are those which can have a substantially liquid state but can be set by cooling or otherwise to form a substantially solid carrier. In a particularly preferred embodiment, the bioabsorbable carrier material, once set, will be essentially stiff or rigid.

In a preferred embodiment of either of the first or second aspects, the carrier is essentially rigid. By "essentially rigid" it is meant that the carrier material should have some structural integrity and be resilient enough for its proposed uses. The carrier material should be substantially non-deflecting or stiff enough to maintain the spacing between the radioactive sources during implantation of the radioactive member into a patient. A molded radioactive member in accordance with the present invention can be stiffer than one made from a braided material such as that described in U.S. Pat. No. 5,460,592. The braided material has been found not to be able to be stiffened enough to prevent jamming according to the scope of physician uses. Jamming may occur when the hollow carrier material used in conventional carriers collapses which may be due, for example, to such long axis strands providing insufficient rigidity or to the overall lack of material. Moreover, where hollow carriers are used, airspaces between the sources may also lead to collapse due to lack of mechanical strength with respect to side compression. The molded carrier material of the present invention substantially improves the properties of the final product in these respects.

Preferably, once in an elongate shape, the bioabsorbable carrier material should be easy to cut using for example a scalpel or the like. Alternatively or additionally, the carrier material may possess preset partially cut or indented points, which facilitate cutting or snapping off of sections of the radioactive member by the clinician.

The bioabsorbable carrier material should also preferably have an appreciable shelf life prior to use, without the need for any special storage or handling conditions. The carrier material should also be sterilisable by any conventional sterilisation method, such as for example using steam, dry heat, ethylene oxide (EtO Gas), electron-beam or gamma-radiation. A preferred sterilization method is treatment with ethylene oxide.

Suitably the bioabsorbable carrier comprises materials which can be molded, for example, poly(glycolic acid) (PGA) and poly(-L-lactic acid) (PLLA), polyester amides of glycolic or lactic acids such as polymers and copolymers of glycolate and lactate, polydioxanone and the like, or combinations thereof. Such materials are more fully described in U.S. Pat. No. 5,460,592 which is hereby incorporated by reference. Suitable commercially available polymers include polyglycaprone 25 (MONCRYL™), polyglactin 910 (VICRYL™) and polydioanone (PDS II), all available from Ethicon, Inc. of New Jersey, U.S.A.

In a particularly preferred embodiment, the carrier material comprises a combination of PLLA (Poly(L-lactide)) and PGA (Poly(glycolide)). Suitably, PLLA and PGA are combined in a ratio of 10/90 w/w (10 parts PLLA, 90 parts PGA). In another embodiment, a polymer of ε-caprolactone could be used. Other suitable combinations will be recognised by those skilled in the art.

Other suitable bioabsorbable polymers and polymer compositions that may be used in this invention are described in the following patents which are hereby incorporated by reference: U.S. Pat. No. 4,052,988 which discloses compositions comprising extruded and oriented filaments of polymers of p-dioxanone and 1,4-dioxepan-2-one; U.S. Pat. No. 3,839,297 which discloses compositions comprising poly[L(-)lactide-co-glycolide] suitable for use as absorbable sutures; U.S. Pat. No. 3,297,033 which discloses the use of compositions comprising polyglycolide homopolymers as absorbable sutures; U.S. Pat. No. 2,668,162 which discloses compositions comprising high molecular weight polymers of glycolide with lactide; U.S. Pat. No. 2,703,316 which discloses compositions comprising polymers of lactide and copolymers of lactide with glycolide; U.S. Pat. No. 2,758,987 which discloses compositions comprising optically active homopolymers of L(-)lactide i.e. poly L-Lactide; U.S. Pat. No. 3,636,956 which discloses compositions of copolymers of L(-)lactide and glycolide having utility as absorbable sutures; U.S. Pat. No. 4,141,087 which discloses synthetic absorbable crystalline isomorphic copolyoxylate polymers derived from mixtures of cyclic and linear diols; U.S. Pat. No. 4,441,496 which discloses copolymers of p-dioxanone and 2,5-morpholinediones; U.S. Pat. No. 4,452,973 which discloses poly(glycolic acid)/poly(oxyalkylene) ABA triblock copolymers; U.S. Pat. No. 4,510,295 which discloses polyesters of substituted benzoic acid, dihydric alcohols, and glycolide and/or lactide; U.S. Pat. No. 4,612,923 which discloses surgical devices fabricated from synthetic absorbable polymer containing absorbable glass filler; U.S. Pat. No. 4,646,741 which discloses a surgical fastener comprising a blend of copolymers of lactide, glycolide, and poly(p-dioxanone); U.S. Pat. No. 4,741,337 which discloses a surgical fastener made from a glycolide-rich blend of polymers; U.S. Pat. No. 4,916,209 which discloses bioabsorbable semi-crystalline depsipeptide polymers; U.S. Pat. No. 5,264,540 which discloses bioabsorbable aromatic polyanhydride polymers; and U.S. Pat. No. 4,689,424 which discloses radiation sterilizable absorbable polymers of dihydric alcohols.

Bioabsorbable polymers and polymer compositions are especially useful when they comprise bioabsorbable fillers such as those described in U.S. Pat. No. 4,473,670 (which is incorporated by reference) which discloses a composition of a bioabsorbable polymer and a filler comprising a poly(succinimide); and U.S. Pat. No. 5,521,280 (which is incorporated by reference) which discloses bioabsorbable polymers and a filler of finely divided sodium chloride or potassium chloride. Such fillers can provide increased mechanical stiffness to bioabsorbable polymers and polymer compositions.

The radioactive member may be of any suitable cross-section, for example substantially circular, substantially circular with at least one flattened surface, or substantially polygonal, for example, square or triangular.

As the bioabsorbable carrier material used in the radioactive member of the present invention is essentially solid, it has a smaller surface area than the equivalent prior art woven or braided materials. It therefore has a lower tendency to swell and cause jamming in the dispensing needle.

Preferably, a carrier according to the present invention will have a smooth outer surface, thus limiting friction with the inside of the dispensing needle, so making jamming of the carrier within the needle due to friction between the needle and the surface of the carrier less likely.

Reduced friction can also be achieved with any cross-section having at least one flat surface e.g. a substantially circular cross-section flattened at a region on the circumference to give a flat surface. Suitable carriers may be triangular or substantially polygonal in shape, for example, hexagonal, octagonal, or 12 or 16-sided etc.

The surface contact between the inner surface of a needle or other delivery device and a carrier of any cross sectional shape can be further minimized by the provision of suitable surface structures on the carrier surface which contacts the delivery device. For example, in the case of a curved carrier surface, surface contact can be reduced by incorporating ridges, spheres or other protrusions in the area of the carrier surface that contacts the needle or delivery device surface. Preferably, these surface structures comprise biocompatible or biodegradable carrier material.

The bioabsorbable carrier can be uniformly or non-uniformly distributed cross-sectionally around the radioactive sources. For example where the sources are substantially cylindrical radioactive seeds, the shape of the cross-section of the internal surface of the carrier is, preferably, substantially round. In an alternative embodiment, the surface is substantially square.

In one embodiment, the carrier of the radioactive member in accordance with either of the first or second aspects forms regions containing radioactive sources and regions devoid of radioactive sources. In a particularly preferred embodiment, the regions of the carrier devoid of radioactive sources will be distinguishable from those regions containing radioactive sources thus enabling a physician to be able to distinguish between the two regions of the carrier. This facilitates the physician being able to make cuts in the elongate bioabsorbable carrier only in those regions between radioactive sources. It is particularly preferred that the regions of the carrier in which radioactive sources are disposed should be wider than those regions where no radioactive source is present In another preferred embodiment, a radioactive member in accordance with either the first or second aspects of the invention is formed by injection molding.

Preferably, the carrier material will be visible using ultrasound imaging techniques i.e. be echogenic. For example, it may comprise sound reflecting particles or bubbles of gas which serve to enhance its ultrasound visibility. Suitable gases include air, nitrogen and carbon dioxide. Preferably, the bubbles are at or near the surface of the carrier.

The carrier material can be uniformly visible or non-uniformly visible by ultrasound. For example, some regions of the carrier may be more visible by ultrasound than other regions. This can arise due to the presence of regions where clusters of sound reflecting gas bubbles or particles reside in a carrier.

The carrier may additionally or alternatively comprise particles which serve to enhance its visibility to ultrasound. Suitable particles include particles of metal (for example titanium or aluminium), glass, silica, iron oxide, sand, clay, plastics such as TEFLON™, porous uniformly-sized non-aggregated particles as described in U.S. Pat. Nos. 5,741,522 and 5,776,496 which are hereby incorporated by reference, hollow microcapsules or solid microspheres such as those disclosed in U.S. Pat. No. 5,648,095 which is hereby incorporated by reference, and microspheres of a fused sugar, a fused amino acid or of PEG (polyethylene glycol).

In an alternative embodiment, the radioactive sources themselves may be rendered visible to ultrasound (i.e. echogenic) by a suitable treatment of the container to introduce grooves or other roughening of the outer surface of a sealed radioactive source such as a seed. See, for example, WO 00/28554 and WO 00/51136.

One advantage of using imaging-visible, for example ultrasound-visible, radioactive members of the invention in brachytherapy is that the signal and image may be read, measured and analysed by suitable computer software sufficiently quickly to allow a physician to plan real-time dosimetry. This is advantageous from a clinical view point for both patient and medical personnel. However, the members of the invention may be used in processes involving any type of dosimetry mapping that uses information obtained due to the imaging visibility of the sources.

In addition, a physician may use the same imaging technique, for example ultrasound, already in place during surgery to confirm both organ (e.g. prostate) position and size, and source placement. This could enable a physician to calculate if additional sources need to be inserted, for example in situations where the dose pattern needs to be recalculated based on the "real" position of the sources.

The overall dimensions of the carrier should be such that it will fit inside a dispensing needle or applicator cartridge. For example, if the internal diameter of a thin walled 18 gauge needle is 0.102 cm (0.040 inches), then the effective maximum diameter of the carrier is preferably less than 0.102 cm (0.040 inches), so that it can be dispensed from within such needles.

Suitably, any conventional radioactive seed may be used as the radioactive source. These include for example the radioactive seeds disclosed in U.S. Pat. Nos. 5,404,309, 4,784,116, 4,702,228, 4,323,055 and 3,351,049 which are hereby incorporated by reference. By "seed" is meant any sealed container, for example a metal container, containing or encapsulating a radioisotope. Suitable biocompatible container materials include metals or metal alloys such as titanium, gold, platinum and stainless steel; plastics such as polyesters and vinyl polymers, and polymers of polyurethane, polyethylene and poly(vinyl acetate); composites such as composites of graphite; glass such as matrices comprising silicon oxide, and any other biocompatible material.

Titanium and stainless steel are preferred materials for the containers.

The radioactive source may also comprise a suitable radioisotope encapsulated within a polymer or ceramic matrix. Typical sources are substantially cylindrical in shape and approximately 4.5 mm long with a diameter of approximately 0.8 mm.

Accordingly, in a preferred embodiment of first or second aspect of the invention the radioactive sources disposed in the radioactive member are brachytherapy sources. Suitably, the radioactive sources are radioactive seeds such as, for example, 6711 seeds available from Medi-Physics, Inc., Arlington Heights, Ill., USA.

Any radioisotope suitable for use in brachytherapy may be used in the source. Non-limiting examples include palladium-103, iodine-125, strontium-89, sulphur-35, cesium-131, gold-198, thulium-170, chromium-56, arsenic-73, yttrium-90, phosphorus-32 and mixtures thereof. Especially preferred are palladium-103 and iodine-125. More than one type of radioisotope may be present in the sources of the invention.

The sources are preferably disposed linearly along the longest axis of the elongate carrier material. The orientation of the sources relative to the carrier will depend on the overall size and shape of the carrier and the sources. If the sources are substantially cylindrical in shape, for example if they are conventional seeds, then they are preferably orientated with their longitudinal axes parallel to the longitudinal axis of the elongate carrier itself. Preferably, the sources are regularly spaced, for example at intervals of between 0.6 and 1.2 cm, preferably at about 1 cm intervals. A known spacing of about 1 cm is preferred if the sources are to be implanted for treatment of prostate cancer. The number of sources used for any particular application will depend on the length of carrier material used. Preferably, the radioactive member is provided as a long strip which can then be cut or snapped to the desired length for a particular application by the medical staff.

Preferably, all the sources in one carrier will contain the same radioisotope and/or be of the same radioactive strength. If more than one type or strength of source is included in one carrier, then the different sources should be arranged in a regular pattern to allow predictable dosing.

In a third aspect of the invention there is provided a method for making a radioactive member in accordance with the first or second aspect of the invention. Suitably, the method comprises the steps of:
a) providing a mold;
b) introducing a plurality of radioactive sources into the mold;
c) introducing liquid bioabsorbable carrier material into the mold;
d) setting the liquid bioabsorbable carrier material; and
e) removing the set product from the mold.

Suitably the mold is elongate i.e. having a length substantially longer than the width.

In a preferred embodiment, the method of the third aspect comprises injection molding. Injection molding is a common technique used for making all manner of plastic parts. It consists of making a metal mold, in which the size and shape of the end product with all other desired characteristics are cut into the metal mold.

For one method of manufacturing of the present invention, a mold is in two halves, with the bottom half having a cut-out of the bottom characteristics of the desired molded product and the top half having a cut-out of the top characteristics. The mold also has holes for the liquid "plastic" to enter the mold. The parts of the mold are brought together such that that the top and bottom halves are aligned properly, then the liquid plastic is injected in. The plastic is then allowed to set (e.g. by cooling) before the parts of the mold are separated and the hardened plastic part is removed from the mold.

Suitably, the mold design for producing a radioactive carrier in accordance with the third aspect of the invention is a three plate vertical mold wherein the liquid carrier material is introduced into the mold through numerous injection ports. Preferably, the three plate mold further comprises a vertical press. Alternative mold designs that achieve the desired result will be recognised by those skilled in the art.

Suitably, the carrier material will be introduced in a molten form. This will typically involve heating the carrier material to its melting point prior to injection into the mold. For example, poly(glycolic acid) has a melting point of either 223° C. or 233° C. (Polymer Handbook, J. Brandrup and E. H. Immergut, 3rd Edition, page VI/61).

In order to produce a radioactive member in accordance with the invention, the mold must preferably allow the position of the radioactive sources within the final product to be predetermined and controllable. Accordingly, in one embodiment of the third aspect, the mold may have a number small of pins protruding inwards towards its centre position so as to hold radioactive sources at predetermined positions in the mold prior to the introduction of the carrier material. Preferably, the small pins are positioned at a spacing which corresponds to the ends of each radioactive source. The mold would be closed with the radioactive sources held in place, and carrier material pumped, or injected, in at each of the injection ports. Preferably, the injection ports would be positioned between each radioactive source, or between every other radioactive source, to ensure that the polymer overmolds the seeds.

In another embodiment of the third aspect, a mold without pins may be used. The radioactive sources could be placed into the mold in a defined spacing prior to injection of the liquid carrier material, the liquid carrier material being introduced into the mold in such a way to cause the radioactive sources (e.g. seeds) to roll, fully immersing the radioactive source in the carrier material.

In still yet another embodiment, the polymer may first be introduced into the mold and the radioactive sources subsequently introduced into the molten polymer. The mold then could be opened and the set carrier material, forming a strand, removed. In this embodiment, steps b) and c) of the method of the third aspect of the invention would be reversed.

Accordingly, there is provided a method comprising the steps of:
a) providing a mold;
b) introducing liquid bioabsorbable carrier material into the mold;
c) introducing a plurality of radioactive sources into the mold;
d) setting the liquid bioabsorbable carrier material; and
e) removing the set product from the mold.

A test tool of 1½ seeds was made to confirm the theoretical filling and molding having a hollowed out area to receive seeds and overmolding to totally encapsulate the seeds in a strand. The carrier medium material was lactide/glycolide co-polymer (polyglactin 910).

Figure 4:
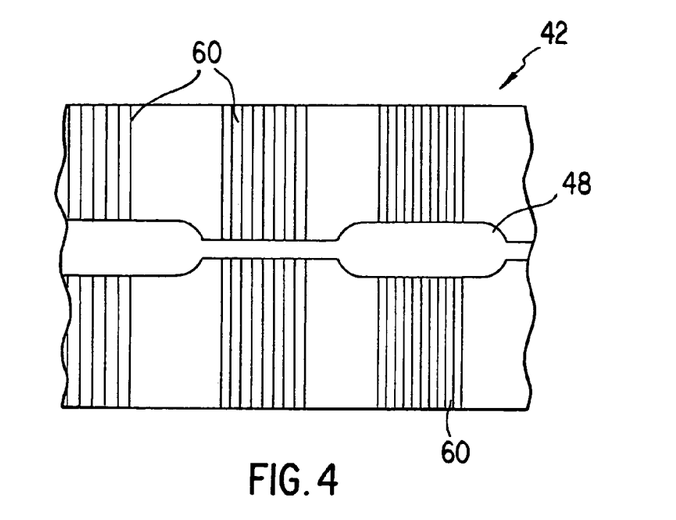
FIG. 4 depicts a back mold plate of the present invention.
Figure 5:
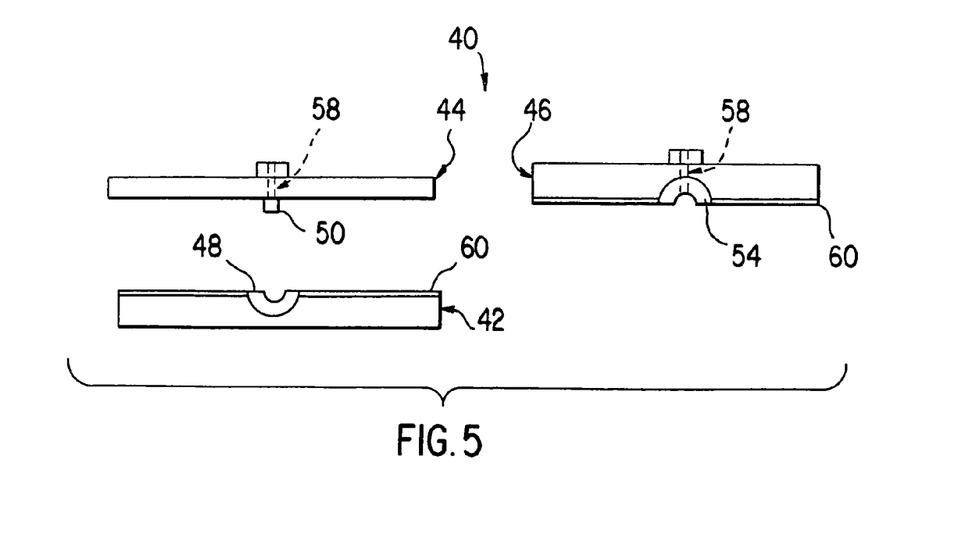
FIG. 5 depicts a three plate mold of the present invention.

A second and larger hand loaded insert mold 40 accommodating 10 seeds and having injection points for the polymer between each seed was also formed. With reference now to FIGS. 4 and 5, mold 40 is a three-plate mold having an elongate base or back mold 42, a seed cavity mold 44, and an encapsulation mold 46. Back mold 42 defines an elongate cavity 48 for receiving the carrier material and forming the lower half portion of an elongate strand of the radioactive member. Cavity 48 is defined so as to form intermediate regions 18 and seed receiving regions 20 in member 10. Seed cavity mold 44 and encapsulation mold 46 are alternatingly employed to fully mold a radioactive member of the present invention.

Seed cavity mold 44 is first placed in registry over back mold 42 to fully enclose cavity 48 for molding the lower half portion of the finished strand. Seed cavity mold 44 includes a plurality of raised protrusions 50, one for each seed 14 to be encapsulated, to extend into cavity 48 for forming a plurality of seed cavities 52, not shown, in the lower half portion of an elongate strand of the radioactive member. Once the lower half portion of the carrier material was formed, seed cavity mold 44 is removed and the radioactive sources 14 are placed in the seed cavities 52 in the lower half portion. Encapsulation mold 46 is then placed in registry over the lower half portion of the carrier material in base mold 42. The encapsulation mold defines a cavity 54 substantially mirroring cavity 48 for receiving the carrier material and thereby fully encapsulate the radioactive sources.

The mold plates desirably defines a number an injection ports 58, shown in phantom lines in FIG. 5, for the seed material about the intermediate regions 20 of a finished radioactive member 10. The mold plates also desirably provide mold vents 60 about the seed receiving regions 18 and intermediate regions 20 of a finished radioactive member 10. Mold venting is technique known in the molding arts for allowing entrapped air to escape a cavity and to better allow the carrier material to flow throughout the mold cavity.

The present invention further contemplates the use of a foaming or blowing method in molding the polymer. Blowing is accomplished by introducing gas bubbles into the polymer. Three common methods are employed to accomplish this are, first, "Whipping" the hot polymer mechanically, second, "Inducting" bubbles into the polymer with pressurized gas, and third, employing a "Blowing Agent". A Blowing Agent is a chemical agent incorporated into the polymer for the purpose of producing gas bubbles to form a foam structure as the carrier material cools that causes bubbles to form in the polymer when heated. For example, sodium bicarbonate releases $CO_2$ gas bubbles upon application of heat in a mold. The cellular structure of the carrier material can be controlled by the amount of bicarbonate added or by the size and structure of the bicarbonate crystals.

The blowing agent will set up a porous structure much like Styrofoam and thereby help to insure better mold filling as the viscosity is decreased. Sodium bicarbonate has been employed as a blowing agent for polyglactin 910 polymer to form molded radioactive members 10 of the present invention. It was found that the sodium bicarbonate, or common baking soda, leaves no residue in the polymer with the exception of $CO_2$, which is a harmless organic substance.

Adding a blowing agent to a polymer of the present invention is desirable for a number of reasons. A blowing agent lowers both the melting temperature of the polymer and the viscosity of the polymer. A blowing agent makes the polymer more rigid and results in the polymer having less surface area on the mold, thereby providing for better mold release. As the resulting structure is more porous, there is a better polymer yield in that less polymer is required to encapsulate the radioactive sources. The porous structure of the carrier also provides for a shorter cooling time post injection, which decreases the manufacturing cycle time and allows for more production in a given time. Furthermore, having less polymer in the carrier material provides for a shorter resorbtion rate of the carrier material into the body.

Further design features of the mold and injection molding process can readily be understood by those skilled in the art. For example, the rate of injection flow is controlled so as to achieve a balanced flow enabling all cavities in the mold to be filled at the approximately same time. The position of the injection ports and rate of filling can be adjusted to ensure a uniform, balanced flow is achieved and that "weld lines" i.e. those regions where adjacent melt-fronts travelling in opposite directions meet and "meld lines" (where two melt fronts flow parallel to each other and create a bond between them) are minimised so as to avoid regions of weakness.

The pressure of injection will be controlled to ensure filling is achieved with a substantially uniform pressure gradient. Most injection molding processes operate at an injection pressure of 100-150 MPa or less.

Other features relevant to the design of the molding process include temperature distribution, wall-shear stress, shear rate, frozen layer fraction, ram speed profile etc. Minimising air traps, variation in volumetric shrinkage and sink index is desirable.

When heated liquid bioabsorbable liquid carrier material is used, setting of the liquid carrier material can be achieved by merely allowing it to cool. Alternatively, setting can be accelerated by the use of coolant flowing around the outside of the mold or through the mold in small manifolds. Balanced cooling is desirable to ensure that shrinkage and warpage are minimised.

The radioactive sources may be positioned in the mold manually or they may be placed in position using an automated process.

In a preferred embodiment, the elongate bioabsorbable carrier (or "strand"), once formed, would go through a heated sizing jig to remove "mold marks" and confirm the size of the final diameter. "Mold marks", or flashing, are little bits of the "plastic" carrier material that are formed at the interface between the two metal mold plates and protrude out of the mold. There is also sometimes a mold mark left by the port where the plastic is introduced.

In another embodiment, a second heating process at the glass transition temperature of the carrier material is performed to enhance the stiffness of the strand. The glass transition temperature is generally much lower than the melting point of the carrier material.

Suitably, surface structures could be formed on the surface of the radioactive member formed in accordance with the method of the third aspect of the invention. A heated mold or press plate, the surface of which is configured as a negative of the structures, could be applied to the carrier. This will cause the carrier surface to have a positive image, reciprocal to the negative image of the mold. Beads or bumps produced on the surface of the carrier can provide reduced contact area and less friction between the carrier and a needle used as a delivery device.

Preferably the method includes rendering the carrier material visible to ultrasound imaging techniques. If the carrier material is a polymer, bubbles of gas may be trapped in the polymer by, for example, blowing bubbles into the polymer prior to injection. Alternatively, the polymer may be agitated (e.g. by sonication) prior to injection under a suitable gas atmosphere such that bubbles of gas are incorporated therein. Suitable gases include air, nitrogen and carbon dioxide.

Alternatively, the carrier material may be subjected to a gas under pressure, for example greater than atmospheric pressure, immediately prior to injection such that the gas becomes dissolved into the material. Upon injection combined with a reduction in the pressure of gas due to warming (such as on injection into an ambient pressure and temperature environment), the gas will expand to form bubbles in the carrier material.

At the end of the manufacturing process, the radioactive member may be cut to suitable lengths and each length loaded separately into a jig, such as the jig disclosed in U.S. Pat. No. 5,460,592. Alternatively, the member may be wound onto a suitable wheel. The jig or wheel may then be shielded and packaged ready for shipping.

Optionally, the radioactive member will be shielded for shipping from the manufacturing site to the site of use. Preferably, after packaging, the product will be sterilized, for example by any conventional sterilisation procedure such as gamma irradiation or ethylene oxide sterilisation. The product can then be shipped from the manufacturer to the site of use as a sterile unit which, once removed from the packaging and shielding, is ready for the member to be used.

The radioactive member may be packaged in any packaging suitable for shipping. A preferred such packaging is a gas-permeable plastic membrane such as a two-part impermeable and permeable plastic bag which pulls apart. Suitable packaging includes Tyvek™ (DuPont). Such permeable packaging permits sterilisation of the radioactive member within the packaging by either ethylene oxide gas (EtO) or autoclaving. A radioactive member of the present invention supplied sterile, within sterile integrity packaging is a preferred embodiment of the present invention.

The radioactive members of the invention may be used in the treatment of a range of conditions including head and neck cancers (including those of the mouth, lips and tongue) brain tumours, lung tumours, cervical tumours, vaginal tumours and prostate cancer. They may be used as a primary treatment (for example in the treatment of prostate cancer or unresectable tumours) or for treatment of residual disease after excision of the primary tumour. They may be used concurrently with, or at the completion of, other treatment modalities, for example external beam radiation therapy, chemotherapy or hormonal therapy.

The radioactive members of the invention may be used alone or in combination with individual radioactive sources, for example seeds.

Thus, as a further aspect of the invention, there is also provided a method of treatment of a condition which is responsive to radiation therapy, for example cancer or arthritis, especially prostate cancer, which comprises the placement of a radioactive member in accordance with the first or second aspect of the invention at or adjacent the site to be treated within a patient for a sufficient period of time to deliver a therapeutically effective dose.

The isotope yttrium-90 may be used for the treatment of pain as it destroys nerve endings. Accordingly, where the radioactive sources contain yttrium-90, there is provided a method for the treatment of pain.

In another embodiment, there is provided a radioactive member in accordance with the first or second aspect of the invention for use in the treatment of cancer or arthritis.

In a preferred embodiment, the radioactive member may be visualised using a suitable imaging technique, preferably ultrasound imaging, in connection with real-time dosimetry equipment.

The radioactive members of the invention may be administered to a patient by placing a suitable length of carrier into the tip of a hollow needle and then placing a stylet into the needle. The needle may be inserted into a patient and then pulled back over the stylet leaving the carrier in place. For methods of administration see, for example, A. van't Riet et al., *Int. J. Radiation Oncology Biol. Phys.*, Vol. 24, pages 555-558, 1992, hereby incorporated by reference.

While the preferred embodiment of the present invention has been shown and described, it will be obvious in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A radioactive member for use in brachytherapy comprising an elongate and essentially rigid bioabsorbable carrier molded about spaced radioactive sources disposed therein, said carrier providing an elongate outer surface of said member, said bioabsorbable carrier defining at least one aperture opening on said elongate outer surface extending in registry with at least one source, said at least one aperture having been imparted to the carrier by the mold used to form the radioactive member.

2. A radioactive member as claimed in claim 1, wherein said elongate bioabsorbable carrier comprises at least one material selected from the group consisting of poly(-L-lactic acid), poly(glycolic acid), polyester amides of glycolic acids, and polyester amides of lactic acids.

3. A radioactive member as claimed in claim 2, wherein said elongate bioabsorbable carrier comprises a combination of PLLA (Poly (L-lactide)) and PGA (Poly (glycolide)) having 10 parts PLLA/90 parts PGA w/w.

4. A radioactive member as claimed in claim 3, wherein said elongate bioabsorbable carrier forms regions containing radioactive sources and regions devoid of radioactive sources.

5. A radioactive member as claimed in claim 4, wherein said regions of said elongate bioabsorbable carrier containing radioactive sources are wider than said regions devoid of radioactive sources.

6. A radioactive member as claimed in claim 1, wherein said elongate bioabsorbable carrier is echogenic.

7. A radioactive member as claimed in claim 1, wherein said radioactive sources are radioactive seeds.

8. A radioactive member as claimed in claim 1, wherein said elongate bioabsorbable carrier comprises a porous structure.

9. A radioactive member for use in brachytherapy comprising an elongate and essentially rigid bioabsorbable carrier with spaced radioactive sources disposed therein, said carrier providing an elongate outer surface of said member, wherein said elongate bioabsorbable carrier is of a substantially solid composition and defines at least one aperture opening on said elongate outer surface in registry with one of said sources.

10. A radioactive member as claimed in claim 9, wherein said elongate bioabsorbable carrier comprises at least one material selected from the group consisting of poly(-L-lactic acid), poly(glycolic acid), polyester amides of glycolic acids, and polyester amides of lactic acids.

11. A radioactive member as claimed in claim 10, wherein said elongate bioabsorbable carrier comprises a combination of PLLA (Poly (L-lactide)) and PGA (Poly (glycolide)) having 10 parts PLLA/90 parts PGA w/w.

12. A radioactive member as claimed in claim 11, wherein said elongate bioabsorbable carrier forms regions containing radioactive sources and regions devoid of radioactive sources.

13. A radioactive member as claimed in claim 12, wherein said regions of said elongate bioabsorbable carrier containing radioactive sources are wider than said regions devoid of radioactive sources.

14. A radioactive member as claimed in claim 9, wherein said elongate bioabsorbable carrier is echogenic.

15. A method of treatment of a condition which is responsive to radiation therapy which comprises the step of placing a radioactive member as claimed in claim 1 adjacent a site to be treated within a patient for a sufficient period of time to deliver a therapeutically effective dose.

16. A method as claimed in claim 15 wherein the condition is cancer.

\* \* \* \* \*